US00PP35554P2

(12) United States Plant Patent
Sisti

(10) Patent No.: US PP35,554 P2
(45) Date of Patent: Dec. 19, 2023

(54) ***ALOCASIA* PLANT NAMED 'GREEN UNICORN'**

(50) Latin Name: ***Alocasia* hybrid**
Varietal Denomination: Green Unicorn

(71) Applicant: Lindsay Sisti, Oak Park, IL (US)

(72) Inventor: Lindsay Sisti, Oak Park, IL (US)

( * ) Notice: Subject to any disclaimer, the term of this patent is extended or adjusted under 35 U.S.C. 154(b) by 0 days.

(21) Appl. No.: 17/803,826

(22) Filed: Dec. 12, 2022

(51) Int. Cl.
*A01H 5/12* (2018.01)
*A01H 6/10* (2018.01)

(52) U.S. Cl.
USPC ..... Plt./373
CPC ..... *A01H 6/10* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Plant Novelty Rights, LLC; James R. Holm

(57) ABSTRACT

A new and distinct *Alocasia* plant named 'Green Unicorn' particularly distinguished by iridescent and lustrous dark greyish green coloration on the adaxial surface of mature leaves, dark red coloration on the abaxial surface of mature leaves, peltate shaped leaves that are slightly bullate between the primary vein and secondary veins on the adaxial surface, light yellow green petioles and stems, compact and dwarf growth habit, and slightly more vigorous growth rate compared to the parents, is disclosed.

3 Drawing Sheets

Figure 1:
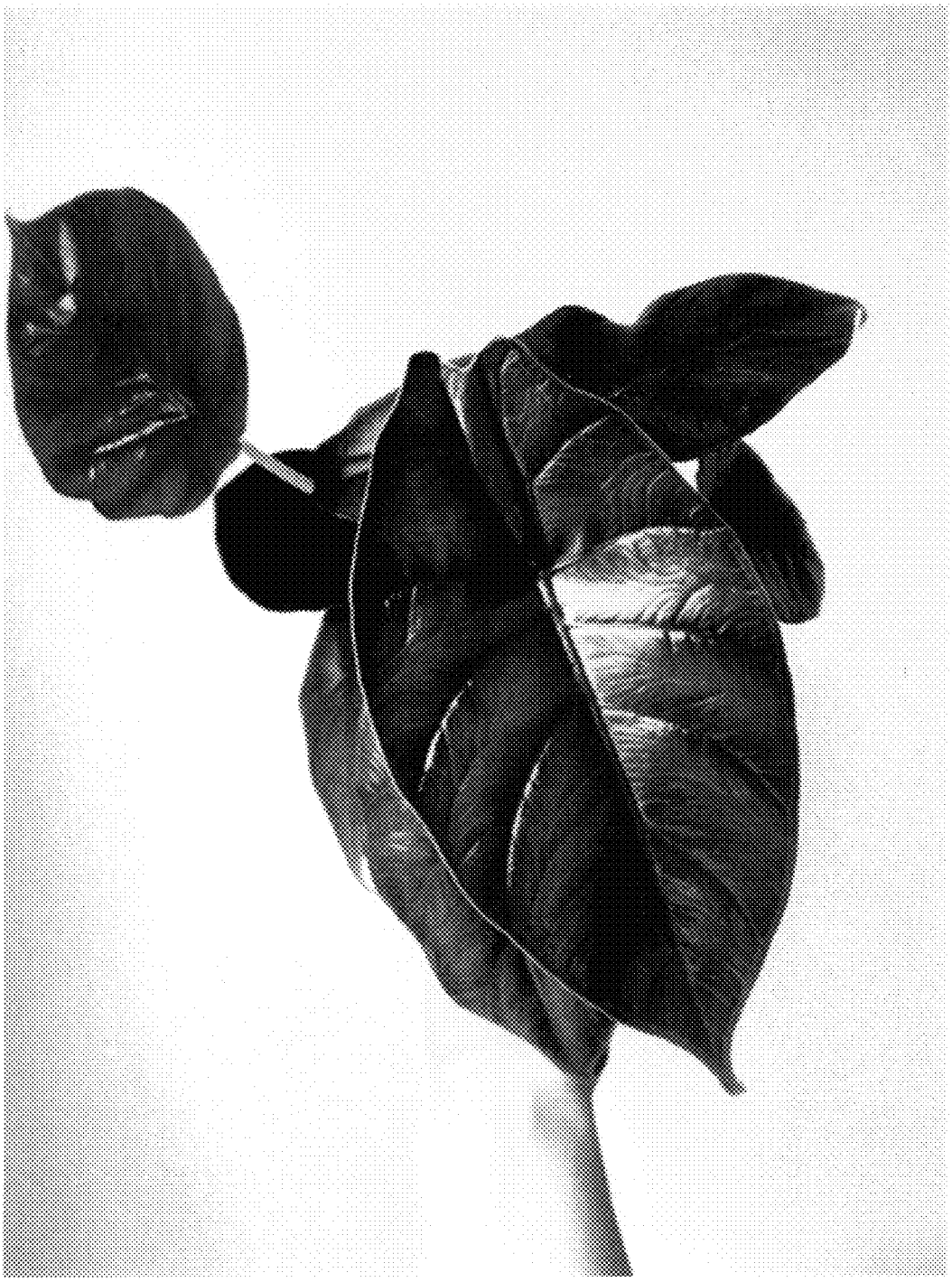

Genus and species: *Alocasia* hybrid.
Variety denomination: 'Green Unicorn'.

BACKGROUND OF THE NEW PLANT

The present invention comprises a new and distinct interspecific hybrid plant of *Alocasia*, hereinafter referred to by its cultivar name 'Green Unicorn'.

The new cultivar was derived from a controlled breeding program conducted by the Inventor in Oak Park, Illinois. The overall purpose of the breeding program is to make new selections of *Alocasia* plants that are compact and have unique and colorful foliage. 'Green Unicorn' is the product of a controlled cross made by the inventor in July 2021 between an unnamed and unpatented *Alocasia azlanii* plant as the female parent and *Alocasia baginda* 'Dragon Scale' (unpatented) as the male parent. Mature berries from said cross were collected in December 2021 through January 2022 and planted in a soilless media. 'Green Unicorn' was selected by the inventor in the spring of 2022 as a single unique plant in Oak Park, Illinois from amongst progeny plants derived from said cross.

The new cultivar was selected based on its distinctive coloration, unique leaf appearance and compact and dwarf growth habit. 'Green Unicorn' was first reproduced asexually from corms in June 2022 in Oak Park, Illinois. Asexual reproduction by corms has shown that the unique features of the new cultivar are stable and reproduced true-to-type in successive generations.

Plant Breeder's Rights for this variety have not been applied for. 'Green Unicorn' has not been made publicly available or sold anywhere in the world prior to the effective filing date of this application.

SUMMARY OF THE INVENTION

The new *Alocasia* cultivar has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Alocasia* cultivar. The combination of these characteristics distinguishes 'Green Unicorn' as a new and distinct cultivar of *Alocasia:*

1. Iridescent and lustrous dark greyish green coloration on the adaxial surface of mature leaves;
2. Dark red coloration on the abaxial surface of mature leaves;
3. Peltate shaped leaves that are slightly bullate between the primary vein and secondary veins on the adaxial surface;
4. Light yellow green petioles and stems;
5. Compact and dwarf growth habit; and
6. Slightly more vigorous growth rate compared to the parents.

DESCRIPTION OF THE PHOTOGRAPHS

This new *Alocasia* cultivar is illustrated by the accompanying-colored photographs which show the overall appearance and distinct characteristics of the plant. The colors shown are as true as can be reasonably obtained by conventional photographic procedures. The photographs are of a 4-month-old plant grown in a 1-quart container inside a growth cabinet under a T8 LED grow light at approximately 75 to 85 degrees F. and under approximately 85 to 90 percent relative humidity in Oak Park, Illinois. Colors in the photographs may differ slightly from the color values cited in the botanical description which accurately describes the colors of the new variety.

Figure 2:
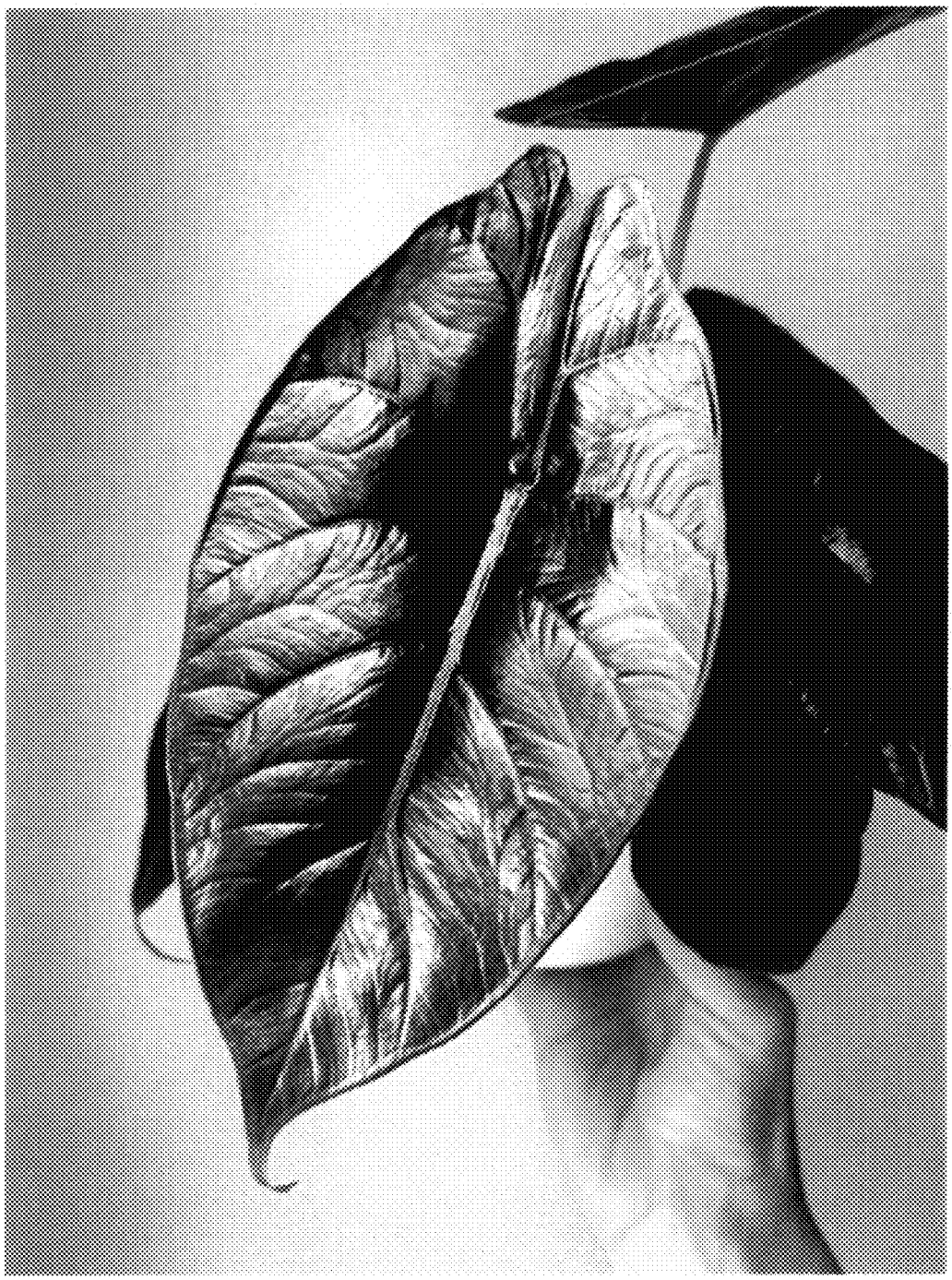

FIG. 1. and FIG. 2. show the overall plant form and foliage of 'Green Unicorn'.

Figure 3:
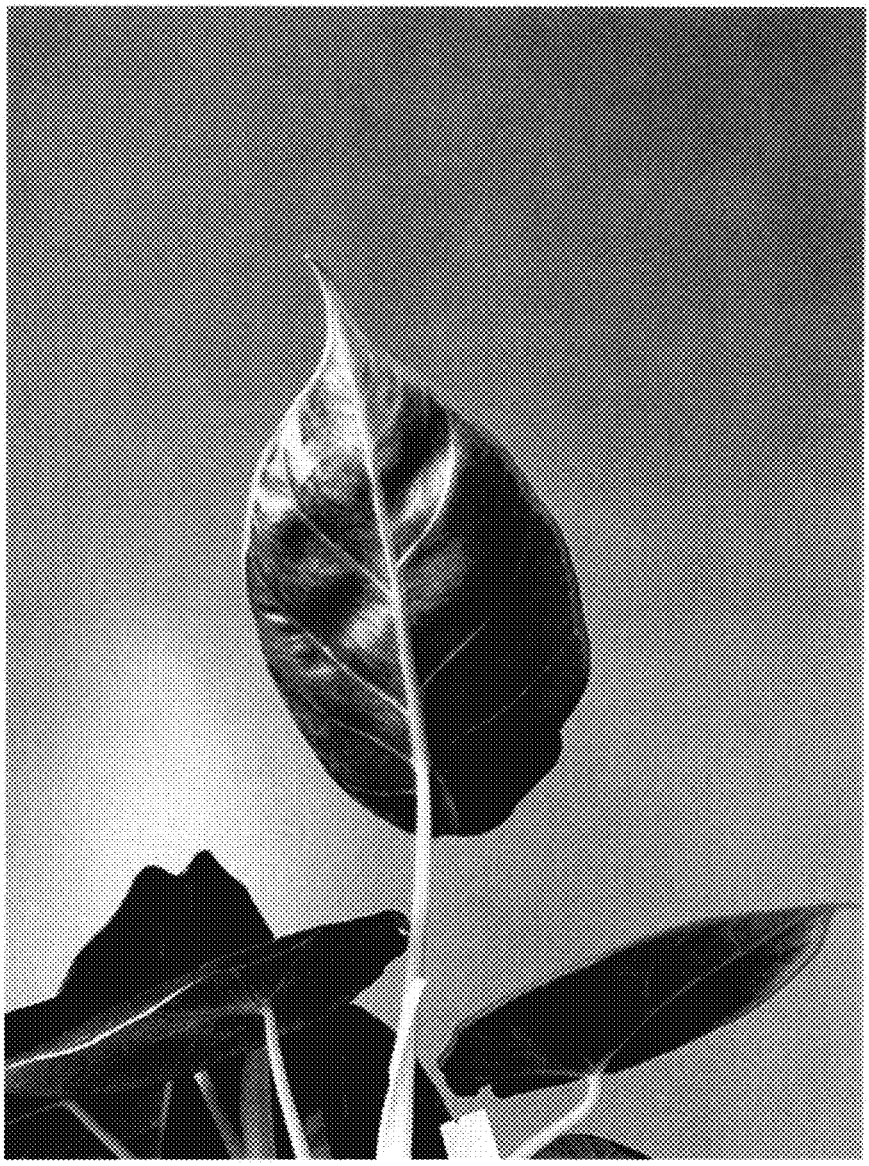

FIG. 3. shows the abaxial surface of mature leaves of 'Green Unicorn'.

DETAILED BOTANICAL DESCRIPTION OF THE PLANT

The following is a detailed description of 4-month-old plants grown in 1-quart containers inside a growth cabinet under a T8 LED grow light at approximately 75 to 85 degrees F. and under approximately 85 to 90 percent relative humidity in Oak Park, Illinois. Observations and measurements were taken in October 2022 under natural light in Mount Dora, Florida. Measurements and numerical values represent averages of typical plant types. Color references are made to The Royal Horticultural Society Colour Chart, Sixth Edition, except where general color terms of ordinary dictionary significance are used.

Classification:

*Family*.—Araceae.

*Botanical*.—*Alocasia* hybrid.

*Common*.—*Alocasia* or Elephant Ear.

*Denomination*.—'Green Unicorn'.

General description:

*Plant type*.—Tropical perennial herb.

*Plant form*.—Open and outwardly arching.

*Growth habit*.—Compact and dwarf.

*Height from soil level to top of foliar plane*.—Approximately 23.5 cm.

*Plant spread*.—Approximately 34.3 cm.

*Primary stem thickness*.—Approximately 2.0 cm in diameter at the base.

*Growth rate*.—Moderate, slightly more vigorous than parents.

*Propagation type*.—Corms.

*Roots*.—Fleshy and fibrous, colored 156D (yellowish white).

*Corms*.—Roughly oval in shape, average of 2.0 cm in length and 1.0 cm in width, translucent in color, 160D (pale yellow), comprised of scales colored 200A (dark greyish reddish brown).

*Time required to produce a young plant from corms*.—Approximately 3.5 to 4 months.

Foliage description:

*Quantity of leaves*.—5.

*Arrangement*.—Whorled.

*Attachment*.—Petiolate.

*Division*.—Simple.

*Lamina*.—Shape and appearance: Peltate, slightly bullate between the primary vein and secondary veins on the adaxial surface. Length: Approximately 22.2 cm when measured along the center axis of the foliar plane. Width: Approximately 12.4 cm at the widest point above the lobes. Orientation: Downwardly nodding. Apex: Caudate, about 2.4 cm in length. Base: Slightly lobate, lobes are about 2.5 cm in width and about 1.9 cm in length; sinus is about 0.64 in width and 1.9 cm in depth. Margins: Slightly undulate. Texture and luster, adaxial surface: Coriaceous, glabrous, and shiny. Texture and luster, abaxial surface: Slightly coriaceous, glabrous, and shiny. Venation pattern: Pinnate, one primary vein (midvein) bifurcating at the base and approximately 12 secondary veins with numerous veinlets appearing in a netted pattern. Color: Juvenile foliage, adaxial surface: Interveinal areas: 146A to 146B (moderate olive green to moderate yellow green) with a blotchy mottling of N144A (strong yellowish green). Primary vein: 147A (moderate olive green). Secondary veins: 147A (moderate olive green). Margin: 144A to 144B (strong yellow green). Basal notch: Slightly 150B (brilliant yellow green). Juvenile foliage, abaxial surface: Interveinal areas: 187B (dark red). Primary vein: 145B (light yellow green). Secondary veins: 145B (light yellow green). Margin: 145A (strong yellow green) and tinged with 187B (dark red). Veinlets: 192B (greenish white). Mature foliage, adaxial surface: Interveinal areas: N189A (dark greyish green). Primary vein: N189A (dark greyish green). Secondary veins: 146B (moderate yellow green). Margin: NN137B (greyish olive green). Mature foliage, abaxial surface: Interveinal areas: 59A (dark red). Primary vein: 145B (light yellow green). Secondary veins: 145B (light yellow green) and slightly tinged with 59A (dark red). Veinlets: 192B (greenish white). Margin: 145B (light yellow green).

*Petioles*.—Strength: Flexible. Orientation: Semi-erect and then overly arching towards the lamina. Length: Approximately 17.5 cm to 19.7 cm. Diameter: Approximately 1.4 cm at the base and narrowing to approximately 0.5 cm at the point of attachment to the lamina. Texture and luster: Glabrous and glossy. Color: Close to 145D (light yellow green) at the base and 145B (light yellow green) out towards the lamina. Wings: Length: Approximately 3.8 cm. Width: Approximately 1.6 cm at the base. Texture and luster: Inner surface: Glabrous and matte. Outer surface: Glabrous and glossy. Color (both inner and outer surfaces): 145C to 145D (light yellow green). Sheath: Length: 6.4 cm. Width: 1.0 cm. Color: 163C (moderate yellow).

Inflorescence:

*Peduncle*.—Length: 8.0 cm. Diameter: 6.0 mm and widening to approximately 8.0 mm at the base of the spadix. Color: 144A (strong yellow green) and lightening to 157C (pale yellow green) at the base of the spadix.

*Spathe*.—Type: Hooded, bract, subtending spadix. Shape: Rotund above female zone, elliptical surrounding female zone. Apex: Aristate. Base: Truncate. Margin: Entire, tinted 184C (moderate purplish red) above female zone. Length: 5.4 cm above female zone, 2.3 cm surrounding female zone. Width/diameter: 3.2 cm in width above female zone and tapering towards the apex, 2.0 cm in diameter surrounding female zone. Color (both inner and outer surfaces): 157B to 157C (pale yellow green) above female zone, 157D (pale yellow green) surrounding female zone.

*Spadix*.—Length: Approximately 6.0 cm. Appendix zone: Shape: Lanceolate. Apex: Narrowly pointed. Length: 3.5 cm. Width: 0.5 mm at widest point near the base and tapering towards the apex. Color: 155A (pale yellow green). Male zone: Shape: Cylindrical. Length: 1.5 cm. Width: 6.0 mm at the widest point near the base and constricting to 5.0 mm near the point of attachment to the base of the appendix zone. Color: NN155D (white). Female zone: Shape: Conical. Length: 1.0 cm. Width: 8.0 mm at the widest point near the base, 5.0 mm just below the male zone. Color: 1B to 1C (greenish yellow).

Cold tolerance: None observed to date.

Disease and pest tolerance: None observed to date.

Fruit and seed set: None observed to date.

Drought tolerance: None observed to date.

COMPARISON WITH PARENTAL VARIETIES

'Green Unicorn' differs from the female parent an unnamed and unpatented *Alocasia azlanii* plant in that 'Green Unicorn' has leaves that are iridescent and dark greyish green on the adaxial surface and dark red on the abaxial surface, whereas the female parent has leaves that are dark coppery purplish green on the adaxial surface and pale green on the abaxial surface. Additionally, 'Green Unicorn' has secondary veins that are moderate yellow green on the adaxial surface, whereas the female parent has distinct secondary veins that are maroon on the adaxial surface. Furthermore, 'Green Unicorn' has leaf veins that are impressed on the adaxial surface with a bullate surface between the veins, whereas the female parent has leaf veins that protrude on both the adaxial and abaxial surfaces.

'Green Unicorn' differs from the male parent *Alocasia baginda* 'Dragon Scale' in that 'Green Unicorn' has glabrous and shiny leaves that are dark greyish green on the adaxial surface and a slightly bullate surface between the veins, whereas the male parent has matte leaves that are dark green and bullae that are pale grey on the adaxial surface. Additionally, 'Green Unicorn' has leaves that are dark red on the abaxial surface with a light yellow green primary vein, whereas the male parent has leaves that are pale green on the abaxial surface with a deep red coloration on the distal portion of the primary vein as well a deep red coloration on the secondary and marginal veins. Furthermore, 'Green Unicorn' has a slightly more compact growth habit and smaller leaf size compared to the male parent. Finally, 'Green Unicorn' has more flexible and thinner glabrous leaves, whereas the male parent has thicker and stiffer coriaceous leaves.

COMPARISON WITH A COMMERCIALLY KNOWN VARIETY

When 'Green Unicorn' is compared to an unnamed and unpatented *Alocasia cuprea* plant, 'Green Unicorn' has leaves that are shiny and dark green and less bullate between the primary and secondary veins, whereas the unnamed and unpatented *Alocasia cuprea* plant has leaves that are more metallic and greenish brown with a suffused pinkish coloration and more strongly bullate between the primary and secondary veins. Additionally, 'Green Unicorn' has a more compact growth habit compared to the unnamed and unpatented *Alocasia cuprea* plant.

I claim:

1. A new and distinct variety of *Alocasia* plant named 'Green Unicorn', substantially as illustrated and described herein.

* * * * *